US010542871B2

(12) United States Patent
Binmoeller et al.

(10) Patent No.: US 10,542,871 B2
(45) Date of Patent: Jan. 28, 2020

(54) SYSTEMS, METHODS AND DEVICES FOR PERFORMING WATER AIDED ENDOSCOPY (71) Applicant: Endeau, Inc., Escondido, CA (US)

(72) Inventors: Kenneth F Binmoeller, Rancho Santa Fe, CA (US); Allen Newman, Rancho Santa Fe, CA (US); Matt Yurek, San Diego, CA (US)

(73) Assignee: Endeau, Inc., Escondido, CA (US)

( * ) Notice: Subject to any disclaimer, the term of this patent is extended or adjusted under 35 U.S.C. 154(b) by 25 days.

(21) Appl. No.: 14/777,393

(22) PCT Filed: Mar. 17, 2014

(86) PCT No.: PCT/US2014/030568
§ 371 (c)(1),
(2) Date: Sep. 15, 2015

(87) PCT Pub. No.: WO2014/145754
PCT Pub. Date: Sep. 18, 2014

(65) Prior Publication Data
US 2016/0038007 A1 Feb. 11, 2016

Related U.S. Application Data (60) Provisional application No. 61/786,520, filed on Mar. 15, 2013, provisional application No. 61/801,427, filed on Mar. 15, 2013.

(51) Int. Cl.
*A61M 35/00* (2006.01)
*A61H 9/00* (2006.01)
(Continued)

(52) U.S. Cl.
CPC ...... *A61B 1/00137* (2013.01); *A61B 1/00163* (2013.01); *A61B 1/04* (2013.01);
(Continued)

(58) Field of Classification Search
CPC .............. A61B 1/31; A61B 17/320016; A61B 1/00137; A61B 1/012; A61B 1/00131
See application file for complete search history.

(56) References Cited

U.S. PATENT DOCUMENTS 5,122,147 A   6/1992 Sewell
6,123,665 A   9/2000 Kawano
(Continued)

FOREIGN PATENT DOCUMENTS

WO   2013018445 A1   2/2013

OTHER PUBLICATIONS

EP14762579.2 Extended European Search Report and Supplementary European Search Report, dated Oct. 11, 2016, 7 pages.
(Continued)

*Primary Examiner* — Anh T Dang
(74) *Attorney, Agent, or Firm* — Scott Davison; Musick Davison LLP (57) ABSTRACT Systems, methods and devices for performing water aided endoscopy (WAE) are provided herein. The systems include a plurality of devices designed to create a sealed environment within the body cavity, including a multi-functional plug, valves, balloons and pumps. The systems also provide specialized tools configured for operation within a liquid environment which are designed to interface with the multi-functional seal for insertion into the body cavity while maintaining the seal, including an adjustable constant shape snare. Additional features of the systems and methods include specialized fluids for increasing visibility with the body cavity, dyes and other solutions for image-enhancement and diagnostics, and software for increasing the clarity of the image in real-time.

6 Claims, 11 Drawing Sheets (51) Int. Cl.
*A61B 1/00* (2006.01)
*A61B 1/04* (2006.01)
*A61B 1/31* (2006.01)
*A61B 17/32* (2006.01)
*A61B 17/3205* (2006.01)

(52) U.S. Cl.
CPC ........ *A61B 1/31* (2013.01); *A61B 17/320016* (2013.01); *A61B 17/32056* (2013.01)

(56) References Cited

U.S. PATENT DOCUMENTS

| | | | |
|---|---|---|---|
| 7,276,075 B1 * | 10/2007 | Callas | A61B 1/00082 600/114 |
| 7,695,428 B2 | 4/2010 | Machida | |
| 2005/0113845 A1 | 5/2005 | Griego et al. | |
| 2005/0124856 A1 | 6/2005 | Fujikura et al. | |
| 2008/0177142 A1 | 7/2008 | Roskopf | |
| 2008/0207994 A1 | 8/2008 | Gonon | |
| 2008/0228034 A1 * | 9/2008 | Fujikura | A61B 1/00082 600/114 |
| 2013/0317515 A1 | 11/2013 | Kuroda et al. | |

OTHER PUBLICATIONS

PCT/US2014/030568, Written Opinion and International Search Report dated Aug. 28, 2014, 4 pages.

* cited by examiner

SYSTEMS, METHODS AND DEVICES FOR PERFORMING WATER AIDED ENDOSCOPY

BACKGROUND

1. Technical Field

The embodiments described herein are related to systems, methods and devices for performing water aided endoscopy (WAE), and more particularly to a multi-functional plug which creates a sealed environment within a body cavity and a plurality of tools for performing an endoscopic procedure therein.

2. Background

Endoscopy is a minimally invasive medical procedure where an endoscope is inserted into a body cavity in order to view the interior of the body cavity. If the body cavity has no orifice to the external environment, an opening must be created through the skin for insertion of the endoscope. If the body cavity has an existing orifice, such as the colon or esophagus, the endoscope can be inserted through the orifice without requiring a separate opening. Once the opening is created, a gas—either air or carbon dioxide—is inserted into the cavity to inflate the body cavity for better viewing by the endoscope. Although endoscopy may be used simply to view the body cavity for diagnostic purposes, one or more tools may be inserted into the body cavity at the same time in order to perform an interventional diagnostic or therapeutic procedure.

Water aided endoscopy (WAE) is a type of endoscopy where the body cavity is filled with water instead of a gas. WAE provides several benefits over gas insufflation, including less distention of the body cavity and image magnification, but also provides significant challenges. While some leakage of air in an endoscopic procedure is expected and does not cause problems, leakage of water from WAE can cause many problems during the procedure, as leaking water may interfere with an individual performing the procedure and must be cleaned up. In addition, many of the tools used during a normal endoscopic procedure may not be suitable for use in a fluidic environment or perform the same way in WAE even if they are suited for exposure to liquid.

SUMMARY

Embodiments described herein provide systems, methods and devices for performing water aided endoscopy (WAE). A plurality of devices may be provided which are designed to create a sealed environment within the body cavity, including a multi-functional plug, valves, balloons and pumps. Specialized tools may also be provided which are configured for operation within a liquid environment and which are designed to interface with the multi-functional plug for insertion into the body cavity while maintaining the seal. Additional features of the systems and methods include specialized fluids for increasing visibility within the body cavity, image-enhancing solutions such as dyes for diagnostics and software for increasing the clarity of the image in real-time.

BRIEF DESCRIPTION OF THE DRAWINGS

The accompanying drawings, which are incorporated in and constitute a part of the specification, illustrate embodiments of the invention and, together with the description, serve to explain the objects, advantages, and principles of the invention. In the drawings.

DETAILED DESCRIPTION

After reading this description it will become apparent to one skilled in the art how to implement the invention in various alternative embodiments and alternative applications. However, all the various embodiments of the present invention will not be described herein. It is understood that the embodiments presented here are presented by way of an example only, and not limitation. As such, this detailed description of various alternative embodiments should not be construed to limit the scope or breadth of the present invention as set forth below.

The systems, methods and devices described herein improve the water aided endoscopy (WAE) process and make it a more effective tool for performing endoscopic procedures. Embodiments described herein primarily focus on performing a colonoscopy, although the principles are applicable to other endoscopic procedures, both rigid (laparoscopy, thoracoscopy) and flexible. There are numerous benefits of WAE including enhanced magnification and visual clarity of tissues immersed in water when being viewed by an endoscope. Furthermore, the fluid filling the colon acts as a lubricant for tools being inserted into the colon, which causes the patient to experience less pain, reduces the amount of anesthesia and therefore reduces the total amount of time required to complete the colonoscopy. In WAE, the colon is not fully distended, which leaves the mucosa, submucosal and muscle layers not stretched tight.

This allows the mucosa to move with respect to the submucosal layers, resulting in reduced risk of perforation of the colon and the ability to visualize more abnormal tissues. Similarly, with a fluid-filled region, the doctor performing the WAE procedure no longer needs to bleb an area where a polyp or lesion needs to be removed, and the risk of perforation from blebbing around scar tissue (which does not separate from the muscle layer) is also reduced. Polyps, lesions, and other tissues can be more easily removed due to their flaccid state in water, as they can be easily moved away from the colon wall before being removed.

In one embodiment, a specialized plug is designed for inserting into the rectum so as to create a seal around the periphery of the rectum and prevent liquid from leaking or spilling during a colonoscopy. Additional devices connected with the plug will also operate to create a seal around the periphery of the opening or hold the plug in place so as to prevent any liquid from leaking out. Specific features of the plug are described further below.

The plug is also configured with one or more openings which allow the controlled passage of water, gas and tools through the plug and into the body cavity without allowing liquid to leak through the openings. The various openings may be of different diameters and positioned at different locations on the plug, as will be set forth below. One or more tubes may connect with respective openings in the plug and protrude from an external surface of the plug to connect with devices to deliver liquid, gas or other materials into the body cavity.

Additional embodiments will be described in detail further herein.

I. Endoscopic Plug

FIGS. 1-4 illustrate one embodiment of an endoscopic plug 100 configured for placement in an opening between a body cavity and an external environment. In a colonoscopy procedure, the plug would be placed in the rectum of a patient. As illustrated in FIGS. 1-4, the plug 100 may include a base pad 102 which is fitted into the opening between the body cavity and the external environment. The distal (100D), or interior end of the plug may include a plug shaft 104 protruding into the body cavity and a balloon mechanism 106 used to create an additional seal, as will be described further below. The proximal (100P), or exterior end of the plug 100 may include a conduit 114 which provides openings with one or more tubes connected with the openings to other mechanisms which deliver gas and/or liquid through the device and into the body cavity or which remove liquid from the body cavity. A central core of the plug 100 is sealably closed with a seal 118 positioned on the proximal side 100P of the base pad to expand and contract in response to the insertion or removal of a tool, so as to create a water-tight environment. A seal cap 116 may be positioned over the seal 118 to hold the seal in place and prevent liquid from spilling out through a scope channel 102C where a tool or optical device is passed into the body cavity.

Figure 2:
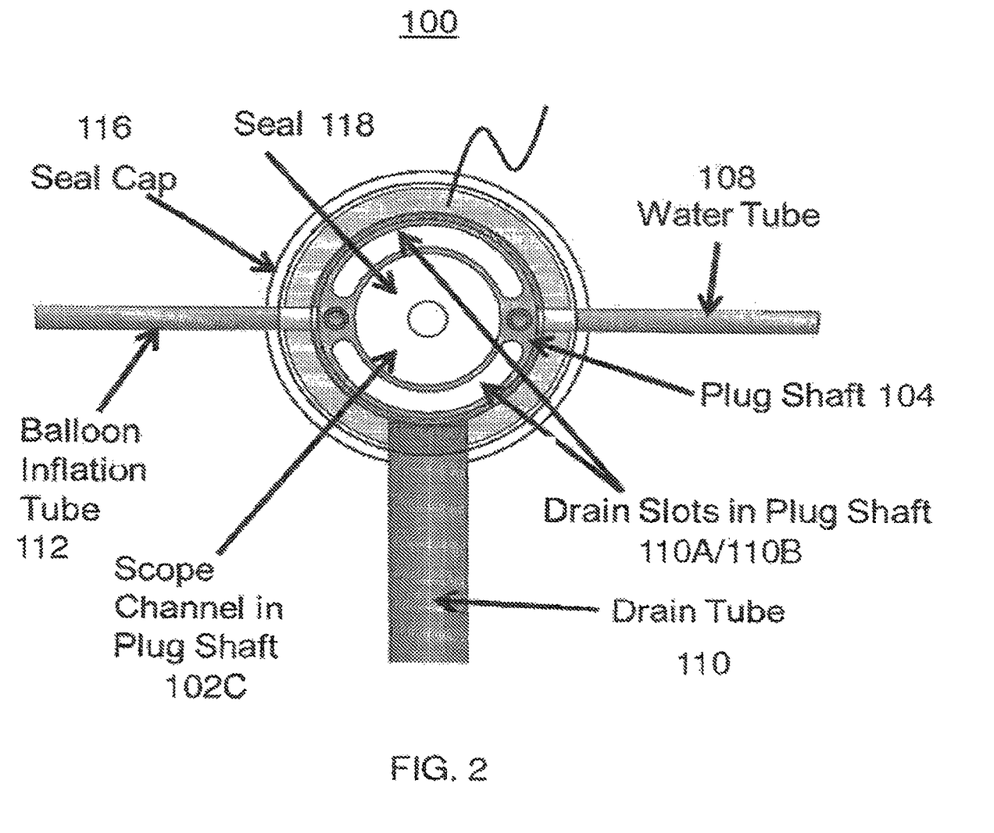
FIG. 2 is a horizontal cross-sectional view of the endoscopic plug, illustrating the design of the plug for input and output of fluid, gas and endoscopic tools, according to one embodiment of the invention.

The plug 100 includes one or more openings designed for input and output of a fluid used to maintain a constant pressure of liquid within the body cavity. In FIG. 2, an input opening in the outer circumference of the shaft may be connected to an input water tube 108 which feeds liquid into the body cavity from a pump. An output tube, or drain tube 110, may be connected with one or more drain slots 110A and 110B, or output openings, to drain liquid from the body cavity. The input water tube 108 and the output drain tube 110 allow a user performing the medical procedure to regulate the pressure inside the body cavity and adjust the pressure if it is too high or low. A pressure regulator or relief valve (not shown) could also be included in the drain line to further control the pressure within the body cavity.

The plug may also include one or more openings for insertion of an endoscopic tool, illustrated as the scope channel 102C in the plug shaft in FIG. 2. The endoscopic tool may be an endoscope with an image capture device that is inserted into the body cavity for capturing images of the body cavity and transmitting the images to a display device in the external environment. The opening of the scope channel 102C may be expandable and re-sealable using the seal 118 so that the tools may be completely removed from the plug without causing liquid to leak out of the body cavity through the tool opening, and expanded to permit a larger tool to pass through. In one embodiment, the input opening for the water tube 108 may be eliminated and integrated into an endoscope tool for pushing water along the shaft of the tool deep into the body cavity. The ability to eject liquid on or near a distal end of the endoscope may prove useful when the user needs to flush away debris or manipulate tissue within the body cavity.

In one embodiment, the output tube 110 and the scope channel opening 102C may be a single opening in order to allow for a larger opening with can accommodate larger tools or multiple tools. Liquid exiting through the centralized output opening and scope channel may be collected in a reservoir disposed on the outside surface of the plug, where the collected liquid is then fed into the drain tube.

Figure 1:
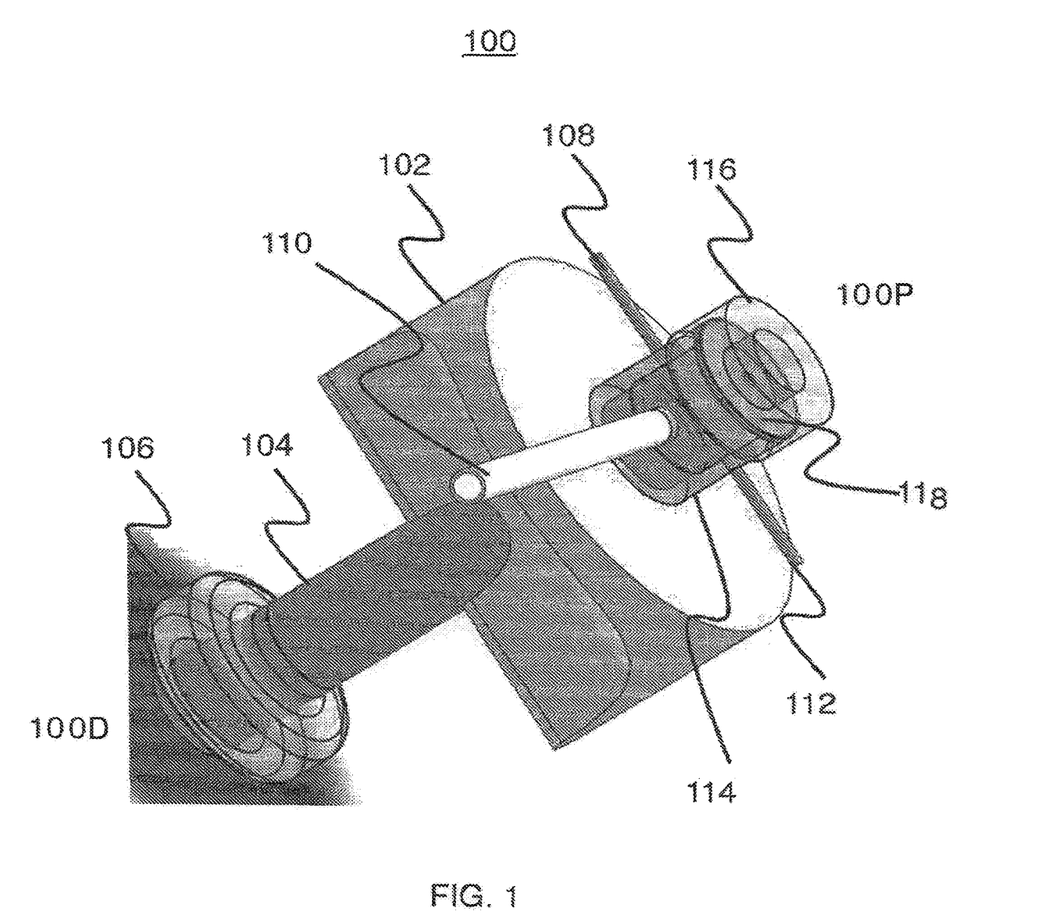
FIG. 1 is a perspective view of an endoscopic plug for use in water aided endoscopy (WAE), according to one embodiment of the invention.
Figure 3:
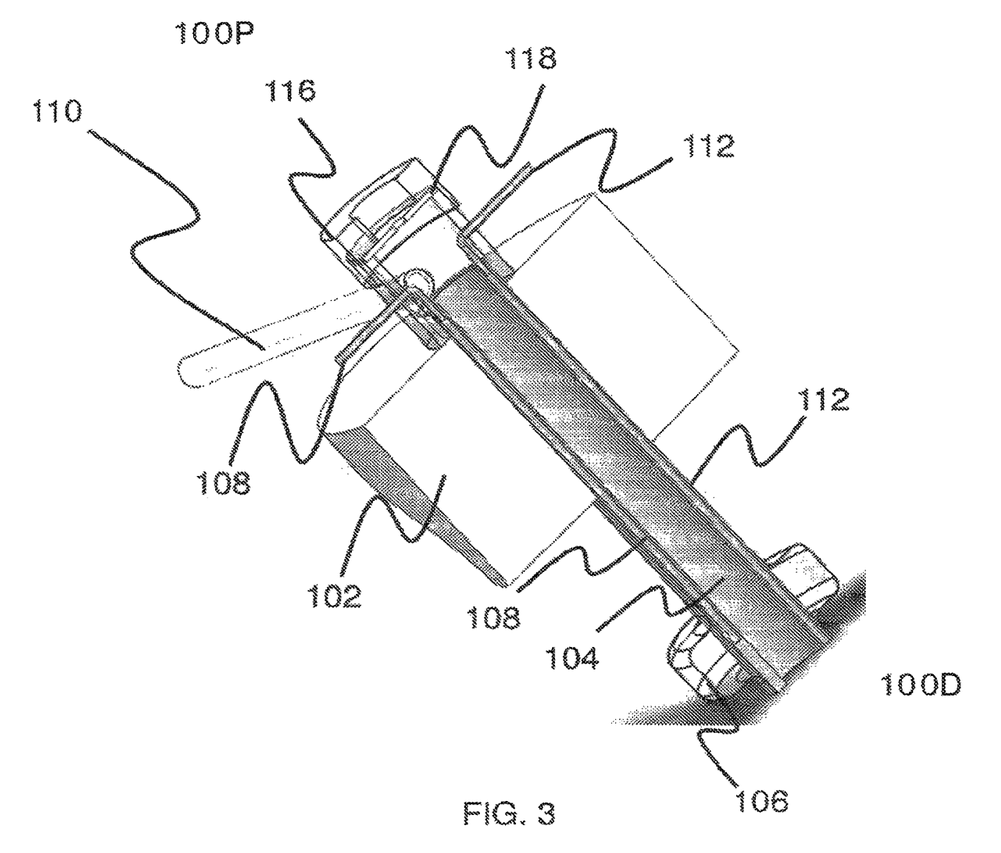
FIG. 3 is a vertical cross-sectional view of the endoscopic plug, illustrating one or more openings for the input and output of the fluid, gas and endoscopic tools, according to one embodiment of the invention.
Figure 4:
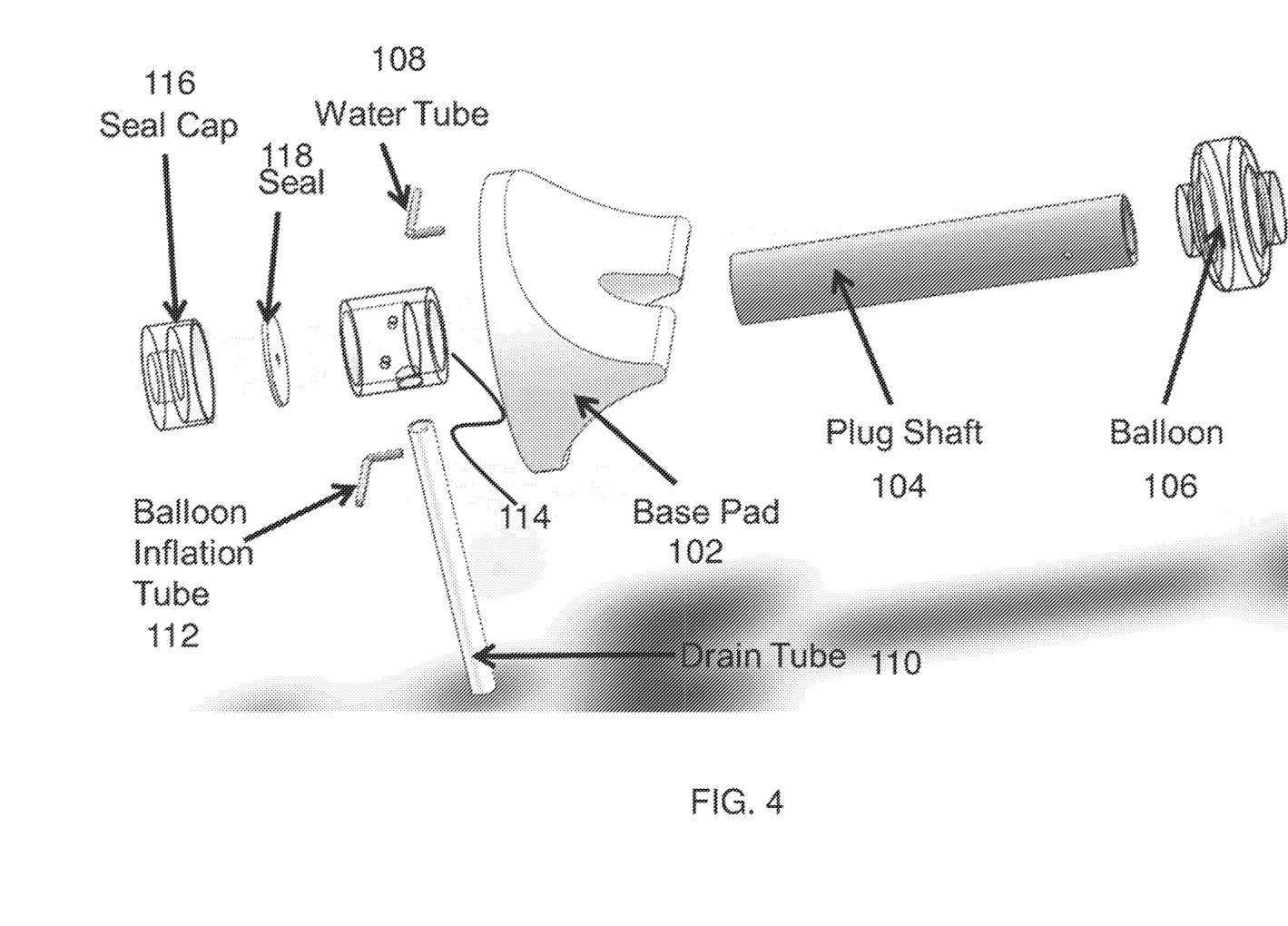
FIG. 4 is an exploded-view of the endoscopic plug, illustrating the design of the components of the plug which provide for the input and output of fluid, a gas and endoscopic tools, according to one embodiment of the invention.

In one embodiment, the plug is configured with an inflatable balloon sealing mechanism 106 which is located on the distal end 100D of the plug, as shown in FIGS. 1, 3 and 4. The balloon 106 may be transparent and provide a better view of the anatomical features surrounding the shaft 104, particularly in comparison with a solid sealing object. An opening in the plug would connect with a balloon inflation tube 112 on the proximal (internal) end 100P of the plug so that air passing into the body cavity through the opening would inflate the balloon 106 once the plug is inserted into the opening in the body cavity. In one embodiment, the balloon 106 could also be inflated with fluid. The inflated balloon 106 is expanded to a diameter larger than the plug so that it is more tightly positioned against the inner wall of the natural or artificially-created orifice than the plug. The inflated balloon 106 is connected with the base pad 102 via the plug shaft 104 and therefore maintains the plug in a more tightly sealed position than the plug does on its own, while also preventing leaks with a pressurized seal. Even though the balloon shown is in a cylindrical shape, it is envisioned that the shape of the balloon can be configured in a different shape to better seal with the internal surface of the body cavity.

In another embodiment, a retention disc may be positioned on the proximal end 100P of the plug in the external environment in order to hold the plug in place from the proximal end. A flexible retention disc may be positioned against the skin of the patient over the top of the plug and be configured to tighten around the skin to hold the plug in place within the body cavity opening. The retention disc may be used separately or in conjunction with the inflatable balloon in order to create a leak-proof seal around the plug.

Figure 10:
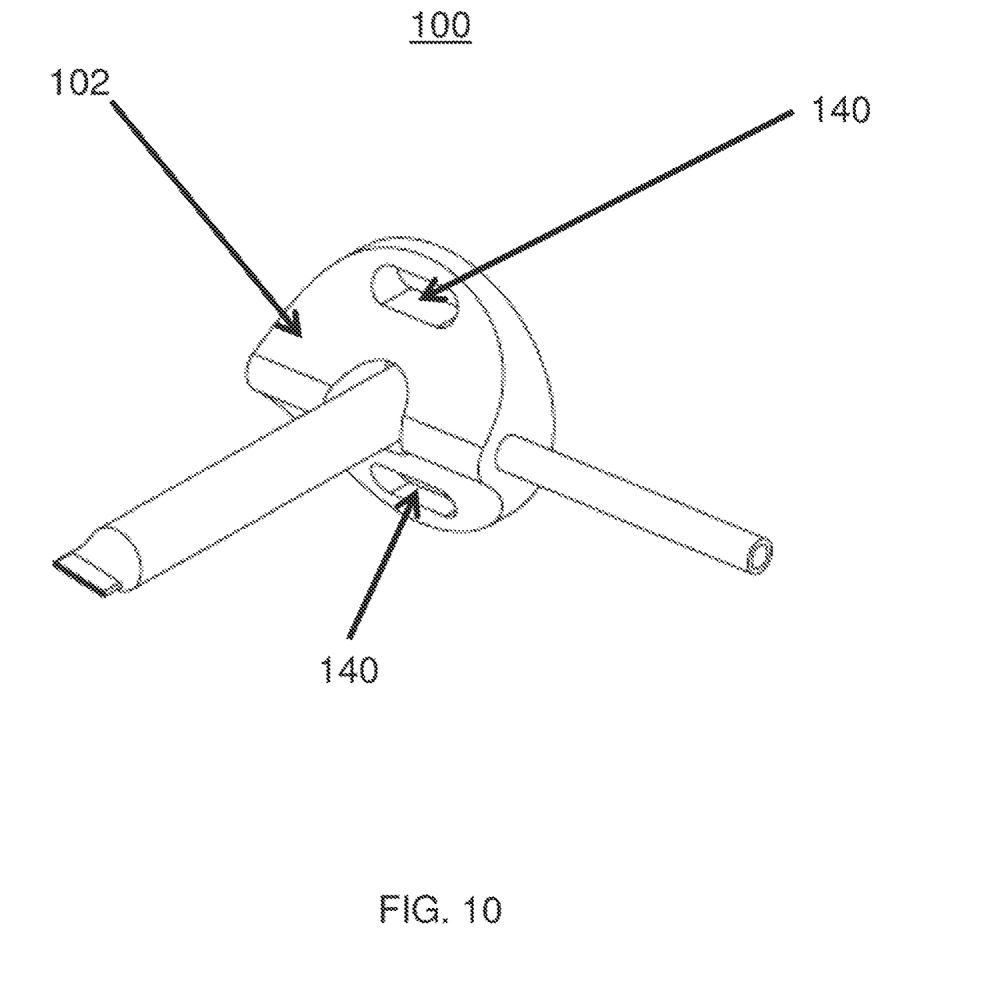
FIG. 10 is a perspective view illustration of a base plug with openings for attaching straps to anchor the plug, according to one embodiment.

In a further embodiment of the plug, the base pad may be held against the rectal opening using straps attached to an external table, or the base pad may be incorporated into an article of clothing worn by the patient during the examination. An illustration of the base pad 102 with openings 140 for attaching the straps is illustrated in FIG. 10. By providing an external mechanism for holding the base pad in place, the plug shaft, balloon and internal expanded seal may be eliminated as a secondary sealing mechanism, which will then allow the physician to view areas of the rectum and colon immediately surrounding the base pad. In this embodiment, a thin membrane (such as latex) may be provided as the sleeve, along with a windsock-type seal, so that tools entering the colon can immediately be accessible within the colon and allow viewing and interaction with the entire colon.

The plug shaft 104 illustrated in FIG. 4 may also operate as a windsock sealing mechanism which collapses when a tool is removed therefrom, maintaining a seal between the body cavity and the external environment.

II. Pressure Valve

In one embodiment, a pressure valve may be used in order to maintain the pressure of the liquid within the body cavity. In one embodiment, the pressure valve may be positioned on the drain tube 110 or the output water opening of the plug to regulate the liquid pressure and maintain an optimal pressure within the body cavity that is advantageous for performing operative procedures, but which does not cause discomfort to the patient or increase to the point that it causes leaks. The valve may be configured to release upon exceeding a certain desired pressure.

In an alternate embodiment, the pressure valve may be positioned within the input opening or within the input water tube 108 and be configured to constrict, fully close or fully open depending on the pressure of the fluid being input into the body cavity.

III. Distal Sealing Mechanism

In one embodiment, a distal sealing mechanism may be provided which is inserted through the plug and positioned at one end of a body cavity distal from the plug (such as the proximal, or upstream end of the colon near the cecum) in order to create a completely sealed environment within a larger body cavity which can be filled with liquid for examination. As previously illustrated in FIGS. 1, 3 and 4, the distal sealing mechanism may be an inflatable balloon 106 which inflates after being inserted into the body cavity (although the balloon would be positioned much further down into the body cavity than that illustrated in FIGS. 1, 3 and 4). The balloon may require a separate input opening and balloon inflation tube 112 in the plug that passes a gas or fluid through the plug (as shown in FIG. 3), through the body cavity and into the balloon at the distal end. Once the balloon 106 is inflated, liquid can be pumped into the artificially created cavity for examination of a specific area.

In another embodiment, a flexible conical-shaped plastic surface like the ones used in percutaneous endoscopic gastrostomy ("PEG") tubes may be used, which contracts for insertion, expands after insertion and tightens as pressure from inside the body cavity pushes on the object.

IV. Pump

In one embodiment, a positive displacement pump is used, such as a roller pump, which allows the user performing the procedure to input more liquid manually as needed. In another embodiment, a continuous flow pump may be used to pump liquid into the body cavity through the plug while ensuring that the liquid has a continuous flow into and out of the body cavity, reducing the risk of high internal pressure which may cause leaks or rupture of tissue. The continuous flow pump may be configured to continually monitor the pressure within the body cavity and adjust the flow of liquid into the body cavity so that the pressure does not exceed or drop below a desired range. If the pressure becomes too great, leakage may occur around the plug or its openings, and the patient may feel discomfort. If the pressure is too low, gas pockets may form or the openings in the body cavity may be too small to move the endoscope and other tools. Software running on a connected computer may control the amount of pressure provided by the continuous flow pump in response to sensors provided in the plug, the valve or the input and output tubes.

V. Tools

In one embodiment, a plurality of endoscopic tools may be configured for insertion through the scope channel 102C of the plug and configured for use within a liquid environment. Endoscopic tools may use cautery (coagulation forceps and probes, snares, knives), enable mechanical cutting (scissors), tissue closure (clips, loops, clamps, stiches), tissue capture (baskets, forceps) and tissue stretching (dilation balloons and bougies). Since the endoscopic tools are operating completely in a liquid environment, some of the tools may require more power in order to achieve a desired coagulation effect or displace the heavier liquid in the body cavity. Other tools may need to be weighted in order to be able to move more easily through the dense liquid.

Other tools may be made more powerful as a result of being in liquid, such as tools which normally produce a great deal of heat. The liquid would more easily dissipate the heat from the tool, allowing the tool to use more power without risking damage or discomfort to the patient. Tools which use electricity or which produce ablative heat may also need to be specifically configured to operate within a liquid environment.

VI. Specialized Liquids

Specially-configured liquids may be used within the body cavity to improve the clarity of the liquid and thus improve the quality of the image captured by the endoscope. In one embodiment, a specialized liquid may be used which increases the refractive index in order to provide a magnification of the image captured inside the body cavity.

In another embodiment, vital and non-vital dyes may be used for chromoscopy and other procedures that will illustrate the flow of liquid within the cavity or attach to certain tissue or anatomical features to highlight potential pathologies. Other solutions such as acetic acid may be used for image enhancement.

Other fluids may be provided for their various colors, densities, surfactants (which eliminate or create bubbles), viscosities, conductivities, etc. In one embodiment, a fluid may be used which expands a submucosa or scar tissue to allow it to separate a polyp, lesion or scar tissue from a lower muscle layer to make it easier to remove.

VII. Image Processing

In one embodiment, the systems and methods for performing WAE include applying image processing algorithms for improving the clarity and quality of images captured by the endoscope. Images taken in a liquid environment may produce unique artifacts and present quality issues not found with images captured in a gas medium. In one embodiment, real-time image enhancement may be performed to improve the clarity of the video images produced by the endoscope and remove artifacts caused by pollutants or other contaminants within the liquid. In one embodiment, an image and video enhancement processor known as the Clarity™ System (Zmed, Inc., San Diego, Calif.) may be used.

VIII. Methods of Use

Figure 9:
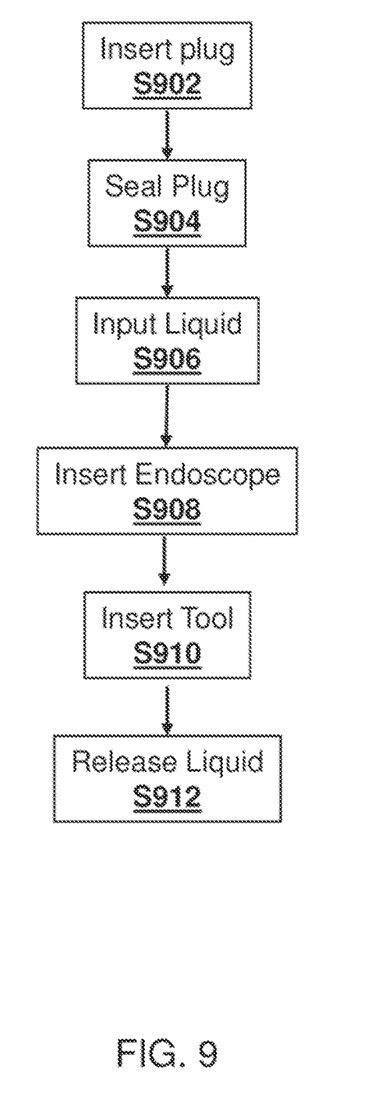
FIG. 9 illustrates a method of performing water-aided endoscopy using the endoscopic plug described herein, according to one embodiment.

A method for performing an endoscopic procedure with the devices described herein is illustrated in FIG. 9, and may include the steps of: inserting a plug into an opening between a body cavity and an external environment (S902); sealing the plug with at least one sealing mechanism (such as the balloon) (S904); inputting a quantity of liquid into the body cavity through an opening in the plug (S906); and inserting at least one endoscope through an opening in the plug (S908). Additional steps may include inserting at least one tool through an opening in the plug (S910); and releasing a quantity of the liquid from the body cavity through an output opening in the plug (S912).

Methods of manufacturing the endoscopic plug device described herein may also be provided for, based on the steps of assembling the parts of the plug and openings along with the connected tubes, seals, shafts, etc.

IX. Alternative Plug Designs

Figure 5:
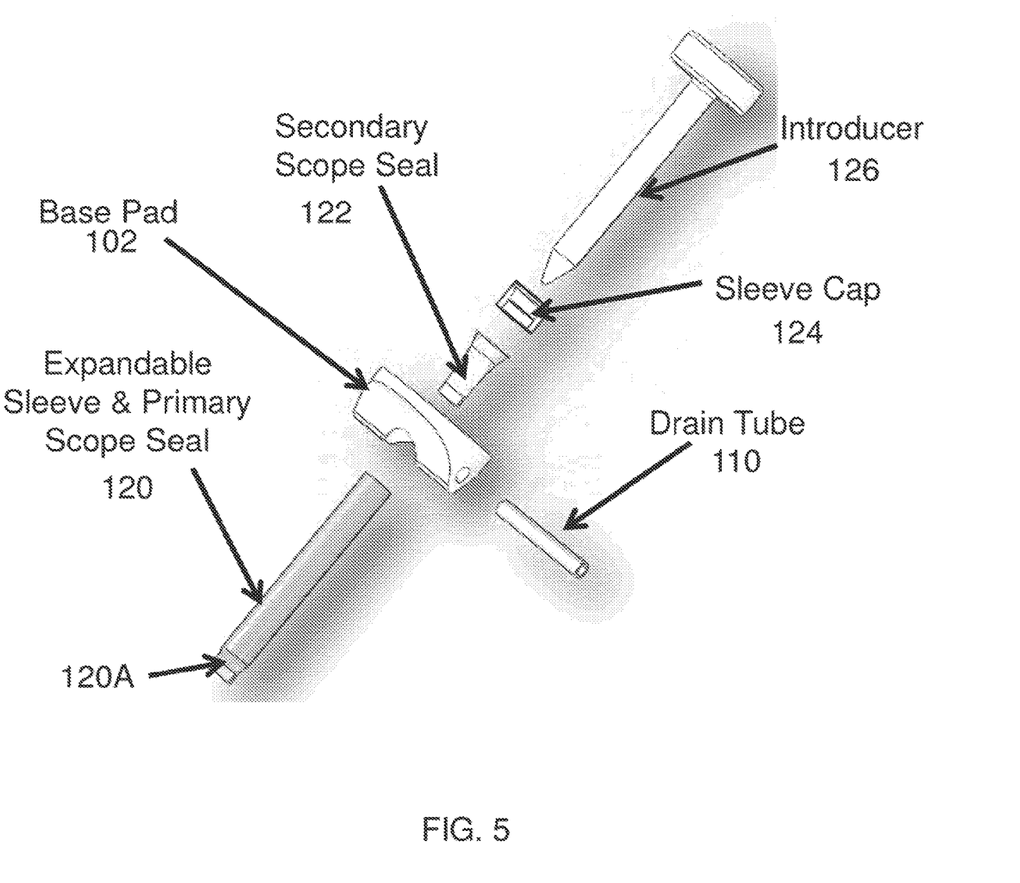
FIG. 5 is an exploded-view illustration of an endoscopic plug with an expandable sleeve, according to a second embodiment of the invention.
Figure 6:
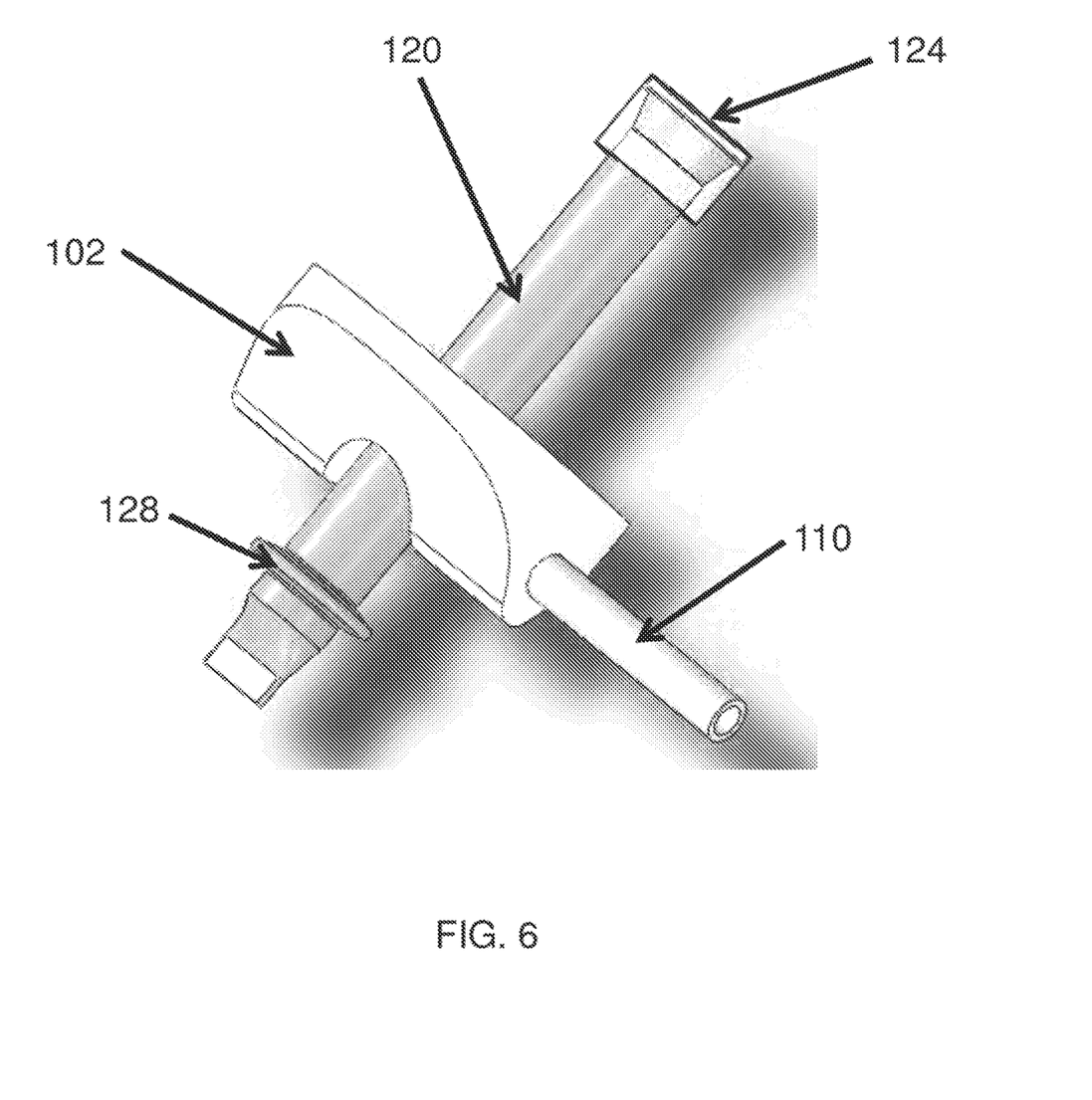
FIG. 6 is a perspective view of the second embodiment of an assembled endoscopic plug with an expandable distal end, according to one embodiment of the invention.
Figure 7:
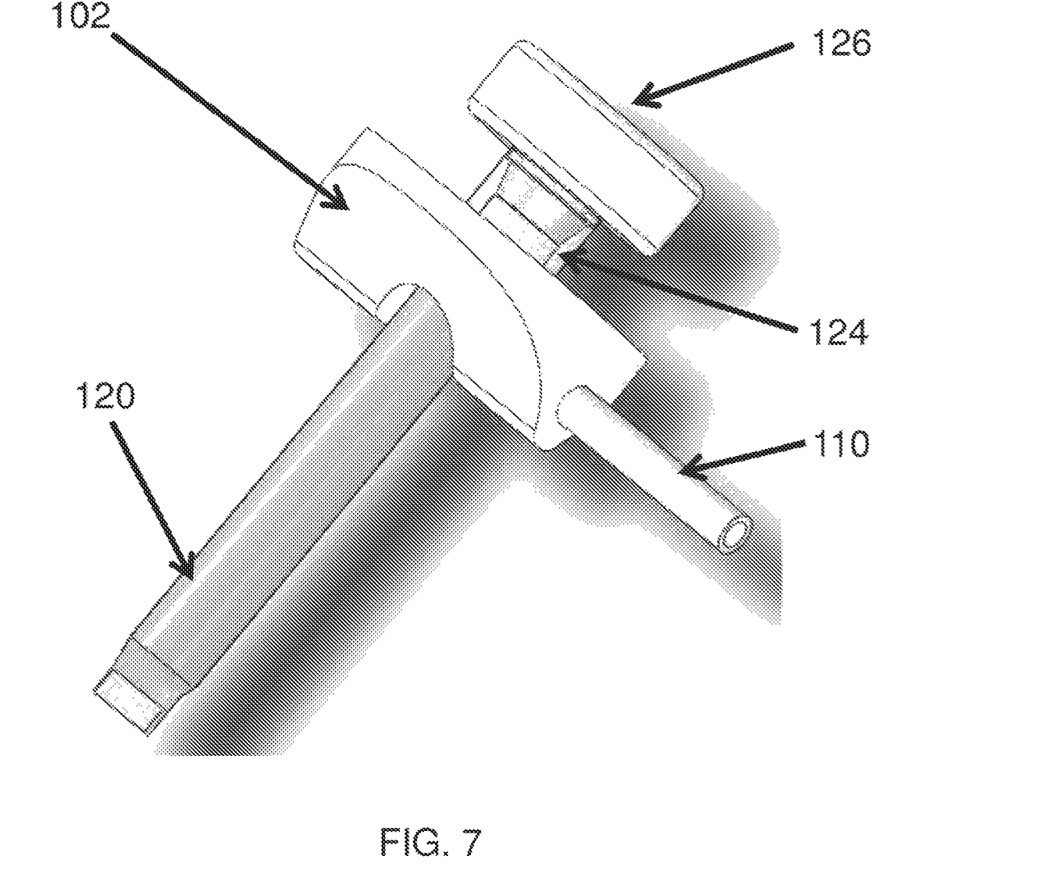
FIG. 7 is a perspective view of the second embodiment of the endoscopic plug that is ready for insertion, according to one embodiment of the invention.

FIGS. 5-7 illustrate an alternative plug design which may also be used for water aided endoscopy (WAE). FIG. 5 is an exploded-view illustration of the alternative plug design, which features an expandable sleeve 120 and primary scope seal 120A, according to a second embodiment of the invention. This alternative plug design does not have a separate water input tube, as water will be input through the primary endoscope opening itself. FIG. 5 also illustrates the other components, such as a secondary scope seal 122 and a sleeve cap 124. The base pad 102 also incorporates a cylindrical drain tube opening 110 to allow fluid pressurized inside the colon to easily and more safely drain out through the drain tube opening, which is then connected with the drain tube. In one embodiment, two "duck bill-style" seals are used at a proximal end and a distal end of the sleeve 120, although only one seal could be used in order to reduce the sleeve's crossing profile for insertion. The distal seal 120A also serves to reduce the profile of the front end of the sleeve.

In this embodiment, a distal end 128 of the expandable sleeve 120 (away from the base pad where the primary scope seal 120A is located) is capable of expanding in a lateral direction around the circumference of the sleeve, as shown in the perspective view illustration of the assembled alternative plug design in FIG. 6. This expandable sleeve 120 provides for the expandable distal end 128 to fit against the interior of the rectal opening. The base pad 102 is positioned to slide onto the outer diameter of the expandable sleeve 120 and slides down on the expandable sleeve until it fits against the outer rectal opening. In other words, when the expanded distal end 128 of the expandable sleeve 120 and the base pad 102 are pulled together, it creates a sealed, locked position around the rectal opening. The sleeve cap 124 may be positioned over the expandable sleeve 120.

FIG. 7 is a perspective view of the second embodiment of the endoscopic plug in an un-sealed position, according to one embodiment of the invention. The movement of the base pad 102 along the sleeve 120 can be illustrated by comparing the location of the base pad between FIG. 6 and FIG. 7, since the base pad 102 is at the proximal end of the plug device.

A method of inserting the plug and sealing it around the rectal opening will now be described. Once the plug has been inserted into the colon, an introducer 126 is removed and the distal end of the expandable sleeve expands and locks (either mechanically or automatically). The sleeve may then be pulled back to seat against the interior rectal wall opening to form an interior portion of the seal. The base pad is then moved forward (toward the rectal opening) while the sleeve is held in place, allowing the base pad to be fitted up against the external rectal opening; thereby fixing the plug in place from both sides.

X. Constant Shape Snare

Figure 8A:
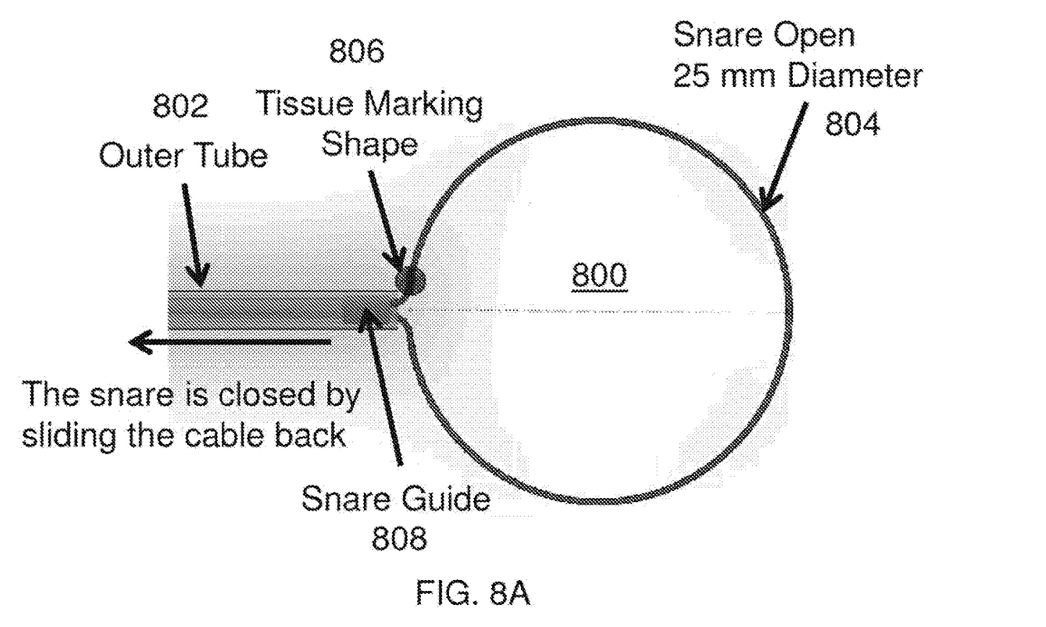
FIGS. 8A-8C are side-view illustrations of a constant-shape snare at a plurality of diameters, according to one embodiment of the invention.
Figure 8B:
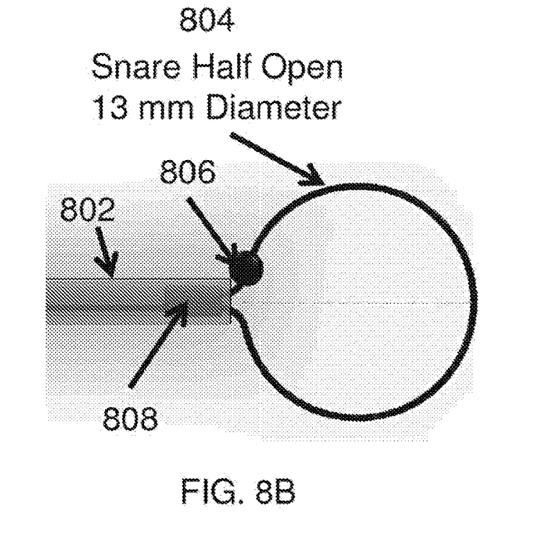
Figure 8C:
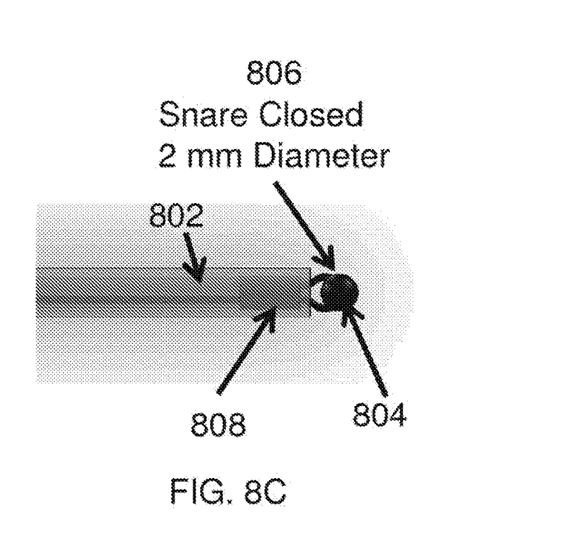

One tool that may be provided for use with the plug in water aided endoscopy is a constant shape snare 800, as illustrated in FIGS. 8A-8C. As shown in FIG. 8A, the constant shape snare includes an outer tube 802 which holds a wire coil 804 which is initially configured in a closed position (see FIG. 8C) for insertion through the plug and then expanded into an open position (see FIG. 8A) for use in removing tissue (such as a polyp on the colon wall). In the open position, the coil 804 forms a circular-shaped loop which is used to grab ("snare") tissue which needs to be examined or removed, and in the closed position, to mark tissue with a coagulation device 806 on the snare. A snare guide 808 guides the wire coil 804 into the outer tube 802, and also serves as an anchor point for the terminal point of the wire coil.

The constant shape snare described herein is capable of maintaining the loop shape as the diameter of the loop expands and contracts, making it easier to snare and remove tissue of any size. The loop may be weighted at a certain portion to maintain a desired angle. Furthermore, the constant shape snare is also configured to maintain the angle or alignment of the loop with respect to the catheter shaft while the loop expands and contracts (such as the half open position of FIG. 8B) so that the angle of the snare with respect to tissue being removed does not change as the size of the loop expands or contracts. The angle is maintained throughout the process of adjusting the size of the loop and even when withdrawing the coil through the outer tube to remove the snare from the plug. This reduces the risk of losing an ensnared polyp or other tissue. In one embodiment, the angle of the snare loop may be adjustable with a moveable core wire, while in another embodiment, a cap on the end of the scope may be provided to help angle the snare in the correct orientation to capture a polyp. The shaft of the snare may also be torqued in order to adjust the orientation of the coil. The coil could be fixed in relation to the shaft and include markings on a proximal end of the shaft visible to the operator to match with the alignment of the coil on the distal end of the shaft. The outer shaft of the catheter may have a braid or coil to provide for the torque to be applied to the snare.

It is desirable when using a snare loop to exert downward pressure on the circumference of the snare while it is closed while preventing it from slipping off at the same time. It is the back (most distal) end of snare that tends to lift and slip off while snare is closed (back end flips up). Some angulation between the snare and shaft may help alleviate slippage, but, in one embodiment, a flexible tent-pole configuration may be used. The pole design would spring open when the snare is opened and push the snare down, while also keeping the back end pressed down. The tent-pole configuration would need to be made of a nonconductive material.

Another embodiment would utilize a cap on the scope which actuates or angles the snare and allows adjustment of the orientation of the snare. There is also the possibility of an additional channel connected to the outer tube that runs along the length of the scope through which the snare can be passed. This would allow the snare to exit more flush with the bowel wall. The working channel is offset from the rim of the endoscope, so it is always exiting at an angle relative to the bowel wall. This design helps achieve the goals of finding a way to keep the snare pressed down against the bowel wall as it closes, preventing the distal end of the snare from flipping up, and maximizing the gripping power of the snare on the mucosa.

In one embodiment, the snare loop may be designed to adjust the angle of orientation as the loop coil moves from the opened position to the closed position in order to increase the likelihood of ensnaring the tissue of interest and maintaining the grip on the tissue as the coil is closed and withdrawn into the outer tube.

Figure 8D:
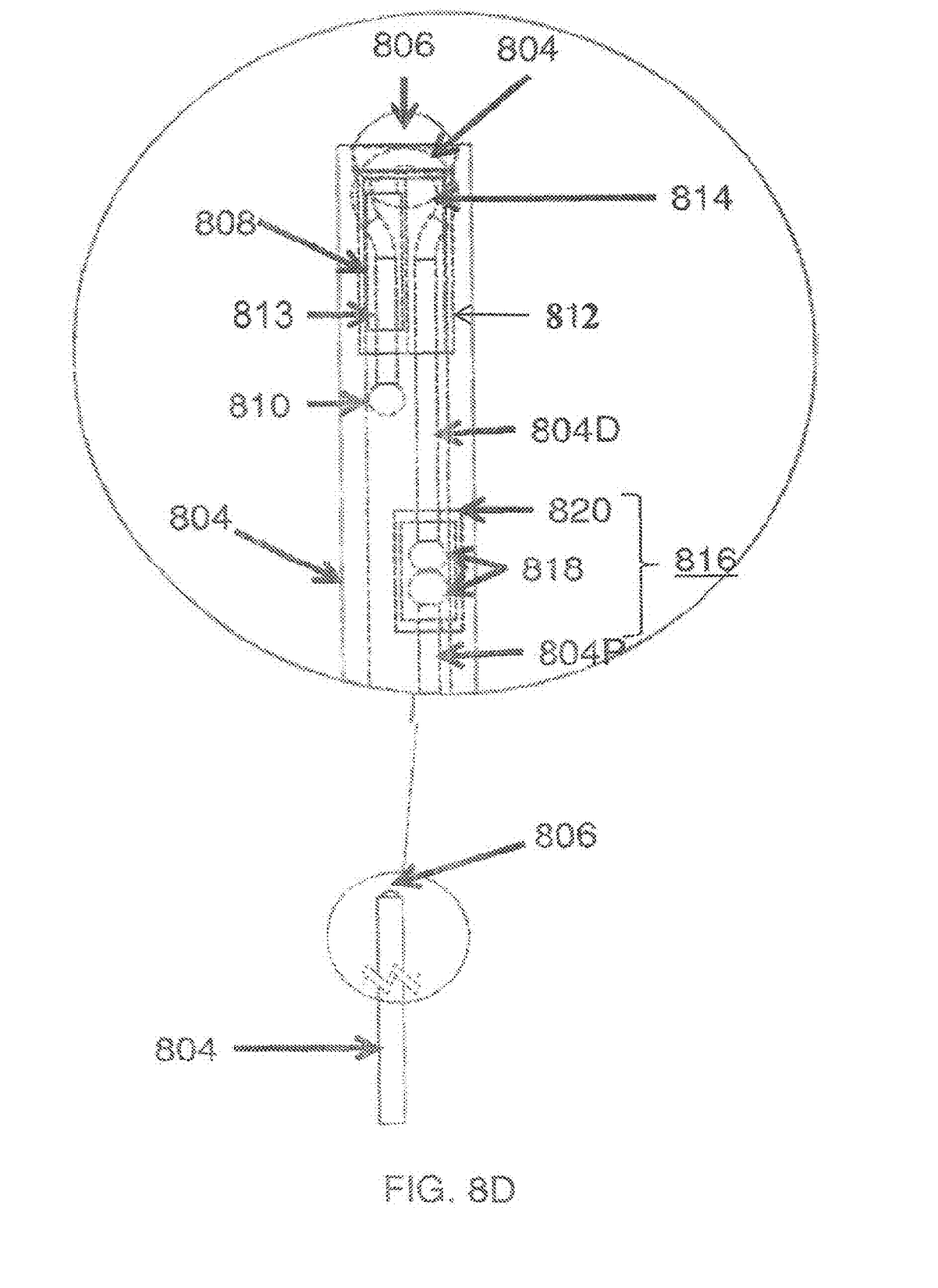
FIGS. 8D is a side view illustration of a swivel mechanism for the constant-shape snare, according to one embodiment of the invention.

FIGS. 8D illustrates one configuration of the constant-shape snare which provides for the snare coil wire to swivel freely to reduce torque created during operation of the snare, thus keeping the snare in the constant shape and angle desired during a procedure. As shown in FIG. 8D, the snare guide 808 may be configured with a housing 812 which houses the terminal point of the coil wire 804, but which has been fastened with a ball swivel 810 which independently rotates while connected with the coil wire and while retaining the coil wire within the housing 812 via retaining tabs 813. As the snare guide 808 is press-fit into the outer tube, this allows the snare wire 804 to swivel independently from the shaft of the snare.

It is important to distinguish the circular shape of the opened snare (FIGS. 8A-C) versus the rounded shape of the closed snare (FIG. 8D). Note that the rounded tip can be used to delivery cautery for both diathermic marking and vessel coagulation for hemostasis or prophylactic ablation. While the concept of a ball to apply cautery (to create a well-demarcated crisp 'dot' as opposed to an ill-defined coagulation blanch that will be difficult to distinguish from cautery artifact after snare resection) is valid, there is concern that there will be an increased amount of cautery delivered at the sphere during snare resection, potentially leading to a deeper wall burn. In one embodiment, a spherical hinged "lid" at the tip of snare which opens when the snare is extruded and closes when snare is retracted into catheter may be utilized, but the snare likely could not be pulled completely into the catheter. It will be rounded and may suffice for marking and coagulation of vessels. However, one alternative design is presented below and illustrated in FIG. 8D.

FIG. 8D illustrates how the tissue coagulation marking device 806 may be retained in a specially-designed conical groove 814 at the end of the snare guide and/or outer tube, to allow for more accurate positioning and use of the tissue coagulation marking device 806 with the coil wire 804 in a closed (retracted) position. Since the tissue coagulation marking device 806 may be a cauterizing tool, the outer tube or snare guide 808 may be configured with an electrical contact point on the conical groove so that the tissue coagulation marking device 806 is powered only when in the groove but is otherwise inert when the coil wire is extended in the circular loop and being used for other purposes. Thus, the ball would be insulated to the snare cable and only be hot when in contact with the insert inside the end of the snare tubing.

FIG. 8D illustrates an alternate rotation mechanism 816 for allowing independent rotation of the coil wire which is positioned further within the snare guide 808. This rotation mechanism utilizes a housing 820 which retains two ball swivels 818 retained on opposite ends thereof, with each ball swivel being connected with one of a proximal coil wire 804P or distal coil wire 804D—the distal coil wire 804D extending distally into the body cavity, while the proximal coil wire 804P extends toward the plug. Swivel loops may be used to connect the coil wires 804 to the ball swivels 818, or the coil wires 804 may be directly connected to the ball swivels 818. This alternate rotation mechanism 816 provides independent rotation of the proximal coil wire 804P within the snare guide and the distal coil wire in the body cavity, again preventing torque from building up and rotating the coil wire into an undesired position.

The constant loop snare is also provided with a tissue marking shape 806, shown in FIG. 8A, for marking areas or effectuating the removal of a polyp or other tissue. The tissue marking shape may be specially configured to function in the water environment, with increased power for marking and a smaller coagulation functionality due to the ability to make cleaner cuts in the water environment. The tissue marking shape 806 is therefore safer and less likely to result in perforations of the tissue or abdominal walls.

FIG. 8A illustrates one embodiment of the constant shape snare in the open configuration with a diameter of approximately 25 millimeters (mm) The snare includes a tissue marking shape. As shown in FIG. 8A, the loop extends from an outer tube of a catheter shaft which is inserted through the opening of the plug. The loop is extended by action of the user outside of the plug feeding more material into the coil area to increase or decrease the size of the loop. In FIG. 8B, the diameter of the loop coil has been reduced to 13 mm, which may be considered a half opening. Finally, FIG. 8C illustrates a loop diameter of approximately 2 mm, where the diameter of the loop coil can be pulled into the outer tube and then extracted from the plug.

The invention claimed is:

1. An endoscopic plug for water aided endoscopy (WAE), comprising:
a base pad at a proximal end of the endoscopic plug, the base pad having an outer surface shaped and configured to create a seal between a body cavity and an external environment;
one or more openings in the base pad configured to allow passage of a fluid between the external environment and the body cavity;
one or more re-sealable openings in the base pad configured to allow insertion of a tool from the external environment into the body cavity;
a plug shaft extending away into the body cavity from the base pad; and
an expandable portion positioned on an outer surface of the plug shaft at a distal end of the endoscopic plug, the expandable portion being shaped and configured to expand to retain the endoscopic plug within the body cavity.

2. The endoscopic plug of claim 1, wherein the one or more openings in the base pad are configured to regulate the pressure of the fluid within the body cavity.

3. The endoscopic plug of claim 1, wherein the fluid lubricates the tool during insertion of the tool into the body cavity.

4. The endoscopic plug of claim 1, further comprising an inflation opening which provides air or fluid to expand the interior expandable portion.

5. The endoscopic plug of claim 1, further comprising a drain tube configured within the endoscopic plug which drains an excess of fluid from within the body cavity.

6. The endoscopic plug of claim 1, wherein the expandable portion is positioned at a fixed distance from the base pad body cavity.

* * * * *